United States Patent [19]

Welter et al.

[11] Patent Number: 4,711,961
[45] Date of Patent: Dec. 8, 1987

[54] BENZISOSELENAZOLETHIONES AND PROCESS FOR THE TREATMENT OF VARIOUS DISEASES IN HUMANS

[75] Inventors: André Welter; Sigurd Leyck, both of Pulheim; Eugen Etschenberg, Cologne, all of Fed. Rep. of Germany

[73] Assignee: A. Nattermann & Cie GmbH, Cologne, Fed. Rep. of Germany

[21] Appl. No.: 705,672

[22] Filed: Feb. 26, 1985

[30] Foreign Application Priority Data

Mar. 1, 1984 [DE] Fed. Rep. of Germany ....... 3407511

[51] Int. Cl.$^4$ ........................................ C07D 293/12
[52] U.S. Cl. ................... 548/121; 544/182; 544/212; 544/238; 544/331; 546/143; 546/159; 546/270
[58] Field of Search ................ 548/121, 209; 514/359, 514/373; 546/143, 159, 270; 544/182, 212, 238, 331

[56] References Cited

U.S. PATENT DOCUMENTS

| | | | |
|---|---|---|---|
| 4,352,799 | 10/1982 | Renson et al. | 424/244 |
| 4,418,069 | 11/1983 | Welter et al. | 424/269 |
| 4,550,168 | 10/1985 | Welter | 546/270 |

FOREIGN PATENT DOCUMENTS 3027084  2/1982  Fed. Rep. of Germany ...... 548/121

OTHER PUBLICATIONS

W. Krause and P. Oehme, Dt.Gesundheitswesen (The German Health Service) 34 (1979) part 36, pp. 1713 to 1718, part 37, pp. 1769 to 1773.
R. Shabana et al., Nouveau Journal de Chimie, vol. 4, (1980) pp. 47 to 51.
R. Lesser and R. Weiss, Berichte der Deutschen Chemischen Gesellschaft, 57 (1924) pp. 1077 to 1082.
A. Ruwet and M. Renson, Bull, Sco. Chim. Belges (1966) 75, pp. 157 to 163.

Primary Examiner—Robert Gerstl
Attorney, Agent, or Firm—Pearne, Gordon, McCoy & Granger

[57] ABSTRACT

The invention relates to new benzisoselenazolethiones of the general formula I

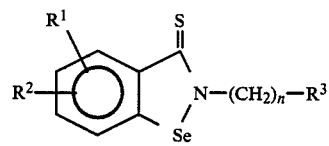

and to processes for the treatment of various diseases by administering them to such beings.

4 Claims, No Drawings

BENZISOSELENAZOLETHIONES AND PROCESS FOR THE TREATMENT OF VARIOUS DISEASES IN HUMANS

The invention relates to new benzisoselenazolethiones, processes for their preparation and their use as an active compound in medicaments for the treatment of inflammatory diseases of the rheumatic type.

The compounds according to the invention correspond to the general formula I

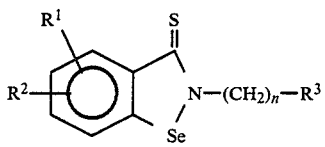

wherein $R^1$ and $R^2$ can be identical or different and independently of one another denote hydrogen, halogen, $C_1$–$C_4$-alkyl, $C_1$–$C_4$-alkoxy, trifluoromethyl or nitro, or $R^1$ and $R^2$ together denote methylenedioxy and n is zero or an integer from 1 to 4, whilst $R^3$ denotes a hydrogen atom, a phenyl group, a phenyl group which is monosubstituted or disubstituted by halogen, alkyl, alkoxy, trifluoromethyl, nitro or methylenedioxy, or a heterocyclic radical with one to four hetero-atoms of the elements nitrogen and/or sulphur, from the group comprising the thiophenes, thiazoles, isothiazoles, imidazoles, pyrazoles, thiadiazoles, pyridines, pyrimidines, pyrazines, pyridazines, benzothiazoles, benzimidazoles, benzotriazines, benzothiophenes, benzothiadiazoles, triazines, triazoles, tetrazoles, quinolines, isoquinolines, indoles and indazoles, it being possible for the heterocyclic radical to be monosubstituted or disubstituted by identical or different substituents from the group comprising halogen, $C_1$–$C_4$-alkyl, $C_1$–$C_4$-alkoxy, mercapto, $C_1$–$C_4$-alkylmercapto, phenyl, nitro and trifluoromethyl.

Preferred compounds are those wherein $R^1$ and $R^2$ can be identical or different and independently of one another denote hydrogen, fluorine, chlorine, methyl, methoxy, nitro and trifluoromethyl or $R^1$ and $R^2$ together denote methylenedioxy and n is zero or an integer from 1 to 4, whilst $R^3$ denotes hydrogen, a phenyl group or a phenyl group which is monosubstituted or disubstituted by fluorine, chlorine, methyl, methoxy, nitro, trifluoromethyl or methylenedioxy, it being possible for the substituents to be identical or different.

Compounds which are additionally preferred are those wherein $R^1$ and $R^2$ can be identical or different and independently of one another denote hydrogen, fluorine, chlorine, methyl, methoxy, nitro or trifluoromethyl or $R^1$ and $R^2$ together denote methylenedioxy and n is zero, whilst $R^3$ denotes a heterocyclic radical with one to four hetero-atoms of the elements nitrogen and/or sulphur, from the group comprising the thiophenes, thiazoles, isothiazoles, imidazoles, pyrazoles, thiadiazoles, pyridines, pyrimidines, pyrazines, benzothiazoles, benzimidazoles, triazines, triazoles and tetrazoles, it being possible for the heterocyclic radical to be monosubstituted or disubstituted by identical or different substituents from the group comprising fluorine, chlorine, methyl, ethyl, butyl, methoxy, ethoxy, mercapto, methylmercapto, ethylmercapto, nitro, phenyl and trifluoromethyl.

Examples of compounds according to the invention are: 2-ethyl-1,2-benzisoselenazole-3(2H)-thione, 6-chloro-2-ethyl-1,2-benzisoselenazole-3(2H)-thione, 6-fluoro-2-ethyl-1,2-benzisoselenazole-3(2H)-thione, 6-methyl-2-ethyl-1,2-benzisoselenazole-3(2H)-thione, 6-methoxy-2-ethyl-1,2-benzisoselenazole-3(2H)-thione, 6-trifluoromethyl-2-ethyl-1,2-benzisoselenazole-3(2H)-thione, 7-methoxy-2-ethyl-1,2-benzisoselenazole-3(2H)-thione, 5-chloro-2-ethyl-1,2-benzisoselenazole-3(2H)-thione, 5-methoxy-2-ethyl-1,2-benzisoselenazole-3(2H)-thione, 5-nitro-2-ethyl-1,2-benzisoselenazole-3(2H)-thione, 4-methoxy-2-ethyl-1,2-benzisoselenazole-3(2H)-thione, 5,6-dichloro-2-ethyl-1,2-benzisoselenazole-3(2H)-thione, 6,7-dichloro-2-ethyl-1,2-benzisoselenazole-3(2H)-thione, 6,7-dimethyl-2-ethyl-1,2-benzisoselenazole-3(2H)-thione, 6,7-methylenedioxy-2-ethyl-1,2-benzisoselenzole-3(2H)-thione, 2-butyl-1,2-benzisoselenazole-3(2H)-thione, 2-(phenylmethyl)-1,2-benzisoselenazole-3(2H)-thione, 2-(4-phenylbutyl)-1,2-benzisoselenazole-3(2H)-thione, 2-phenyl-1,2-benzisoselenazole-3(2H)-thione, 6-chloro-2-phenyl-1,2-benzisoselenazole-3(2H)-thione, 6-fluoro-2-phenyl-1,2-benzisoselenazole-3(2H)-thione, 6-methyl-2-phenyl-1,2-benzisoselenazole-3(2H)-thione, 6-methoxy-2-phenyl-1,2-benzisoselenazole-3(2H)-thione, 6-trifluoro-methyl-2-phenyl-1,2-benzisoselenazole-3(2H)-thione, 7-methoxy-2-phenyl-1,2-benzisoselenazole-3(2H)-thione, 5-chloro-2-phenyl-1,2-benzisoselenazole-3(2H)-thione, 5-methoxy-2-phenyl-1,2-benzisoselenazole-3(2H)-thione, 5-nitro-2-phenyl-1,2-benzisoselenazole-3(2H)-thione, 4-methoxy-2-phenyl-1,2-benzisoselenazole-3(2H)-thione, 5,6-dichloro-2-phenyl-1,2-benzisoselenazole-3(2H)-thione, 6,7-dichloro-2-phenyl-1,2-benzisoselenazole-3(2H)-thione, 6,7-methylenedioxy-2-phenyl-1,2-benzisoselenazole-3(2H)-thione, 2-(2-fluorophenyl)-1,2-benzisoselenazole-3(2H)-thione, 2-(3-fluorophenyl)-1,2-benzisoselenazole-3(2H)-thione, 2-(4-fluorophenyl)-1,2-benzisoselenazole-3(2H)-thione, 2-(2-chlorophenyl)-1,2-benzisoselenazole-3(2H)-thione, 2-(3-chlorophenyl)-1,2-benzisoselenazole-3(2H)-thione, 2-(4-chlorophenyl)-1,2-benzisoselenazole-3(2H)-thione, 2-(2-trifluoromethylphenyl)-1,2-benzisoselenazole-3(2H)-thione, 2-(3-trifluoromethylphenyl)-1,2-benzisoselenazole-3(2H)-thione, 2-(4-trifluoromethylphenyl)-1,2-benzisoselenazole-3(2)-thione, 2-(2-methylphenyl)-1,2-benzisoselenazole-3(2H)-thione, 2-(3-methylphenyl)-1,2-benzisoselenazole-3(2H)-thione, 2-(4-methylphenyl)-1,2-benzisoselenazole-3(2H)-thione, 2-(2-methoxyphenyl)-1,2-benzisoselenazole-3(2H)-thione, 2-(3-methoxyphenyl)-1,2-benzisoselenazole-3(2H)-thione, 2-(4-methoxyphenyl)-1,2-benzisoselenazole-3(2H)-thione, 2-(2,4-dimethoxyphenyl)-1,2-benzisoselenazole-3(2H)-thione, 2-(2,5-dimethoxyphenyl)-1,2-benzisoselenazole-3(2H)-thione, 2-(3,4-dimethoxyphenyl)-1,2-benzisoselenazole-3(2H)-thione, 2-(3,5-dimethoxyphenyl)-1,2-benzisoselenazole-3(2H)-thione, 2-(2,3-dimethylphenyl)-1,2-benzisoselenazole-3(2H)-thione, 2-(2,4-dimethylphenyl)-1,2-benzisoselenazole-3(2H)-thione, 2-(2,5-dimethylphenyl)-1,2-benzisoselenazole-3(2H)-thione, 2-(2,6-dimethylphenyl)-1,2-benzisoselenazole-3(2H)-thione, 2-(3,4-dimethylphenyl)-1,2-benzisoselenazole-3(2H)-thione, 2-(3,5-dimethylphenyl)-1,2-benzisoselenazole-3(2H)-thione, 2-(2-chloro-4-methylphenyl)-1,2-benzisoselenazole-3(2H)-thione, 2-(2-chloro-6-methylphenyl)-1,2-benzisoselenazole-3(2H)-thione, 2-(3-chloro-2-methylphenyl)-1,2-benzisoselenazole-3(2H)-thione, 2-(3-chloro-4-methylphenyl)-1,2-benzisoselenazole-3(2H)-thione, 2-(4-chloro-2-methylphenyl)-1,2-benzisoselenazole-3(2H)-thione, 2(5-chloro-2-methylphenyl)-1,2-benzisoselenazole-3(2H))-thione, 2-(5-fluoro-2-methylphenyl)-1,2-benzisoselenazole-3(2H)-thione, 2-(4-fluoro-3-methylphenyl)-1,2-benzisoselenazole-3(2H)-thione, 2-(4-fluoro-2-methylphenyl)-1,2-benzisoselenazole-3(2H)-thione, 2-(3-fluoro-4-methylphenyl)-1,2-benzisoselenazole-3(2H)-thione, 2-(2-fluoro-4-methylphenyl)-1,2-benzisoselenazole-3(2H)-thione, 2-(3-chloro-4-fluorophenyl)-1,2-benzisoselenazole-3(2H)-thione, 2,-(4-chloro-3-fluorophenyl)-1,2-benzisoselenazole-3(2H)-thione, 2-(2-nitrophenyl)-1,2-benzisoselenazole-3(2H)-thione, 2-(3-nitrophenyl)-1,2-benzisoselenzole-3(2H)-thione, 2-(4-nitrophenyl)-1,2-benzisoselenazole-3(2H)-thione, 2-(4-methoxy-2-nitrophenyl)-1,2-benzisoselenazole-3(2H)-thione, 2-(2-methyl-4-nitrophenyl)-1,2-benzisoselenazole-3(2H)-thione, 2-(4-methyl-2-nitrophenyl)-1,2-benzisoselenazole-3(2H)-thione, 2-(2-methyl-3-nitrophenyl)-1,2-benzisoselenazole-3(2)-thione, 2-(2-methyl-5-nitrophenyl)-1,2-benzisoselenazole-3(2H)-thione, 2-(3,4-methylendioxyphenyl)-1,2-benzisoselenazole-3(2H)-thione, 2-(2-pyridyl)-1,2-benzisoselenazole-3(2H)-thione, 2-(3-pyridyl)-1,2-benzisoselenazole-3(2H)-thione, 2-(4-pyridyl)-1,2-benzisoselenazole-3(2H)-thione, 6-chloro-2-(2-pyridyl)-1,2-benzisoselenazole-3(2H)-thione, 6-fluoro-2-(2-pyridyl)-1,2-benzisoselenazole-3(2H)-thione, 6-methyl-2-(2-pyridyl)-1,2-benzisoselenazole-3(2H)-thione, 6-methoxy-2-(2-pyridyl)-1,2-benzisoselenazole-3(2H)-thione, 6-trifluoromethyl-2-(2-pyridyl)-1,2-benzisoselenazole-3(2H)-thione, 7-methoxy-2-(2-pyridyl)-1,2-benzisoselenazole-3(2H)-thione, 5-chloro-2-(2-pyridyl)-1,2-benzisoselenazole-3(2H)-thione, 5-methoxy-2-(2-pyridyl)-1,2-benzisoselenazole-3(2H)-thione, 5-nitro-2-(2-pyridyl)-1,2-benzisoselenazole-3(2H)-thione, 4-methoxy-2-(2-pyridyl)-1,2-benzisoselenazole-3(2H)-thione, 5,6-dichloro-2-(2-pyridyl)-1,2-benzisoselenazole-3(2H)-thione, 6,7-dichloro-2-(2-pyridyl)-1,2-benzisoselenazole-3(2H)-thione, 6,7-methylenedioxy-2-(2-pyridyl)-1,2-benzisoselenazole-3(2H)-thione, 2-(2-chloro-3-pyridyl)-1,2-benzisoselenazole-3(2H)-thione, 2-(2-methoxy-5-pyridyl)-1,2-benzisoselenazole-3(2H)-thione, 2-(3-nitro-2-pyridyl)-1,2-benzisoselenazole-3(2H)-thione, 2-(5-nitro-2-pyridyl)-1,2-benzisoselenzole-3(2H)-thione, 2-(3-methyl-2-pyridyl)-1,2-benzisoselenazole-3(2H)-thione, 2-(4-methyl-2-pyridyl)-1,2-benzisoselenazole-3(2H)-thione, 2-(5-methyl-2-pyridyl)-1,2-benzisoselenazole-3(2H)-thione, 2-(6-methyl-2-pyridyl)-1,2-benzisoselenazole-3(2H)-thione, 2-(3,5-dichloro-2-pyridyl)-1,2-benzisoselenazole-3(2H)-thione, 2-(2,6-dichloro-3-pyridyl)-1,2-benzisoselenazole-3(2H)-thione, 2-(4,6-dimethyl-2-pyridyl)-1,2-benzisoselenazole-3(2H)-thione, 2-(5-chloro-2-pyridyl)-1,2-benzisoselenazole-3(2H)-thione, 2-(4-chloro-2-pyridyl)-1,2-benzisoselenazole-3(2H)-thione, 2-(2-pyrimidinyl)-1,2-benzisoselenazole-3(2H)-thione, 6-chloro-2-(2-pyrimidinyl)-1,2-benzisoselenazole-3(2H)-thione, 6-fluoro-2-(2-pyrimidinyl)-1,2-benzisoselenazole-3(2H)-thione, 6-methyl-2-(2-pyrimidinyl)-1,2-benzisoselenazole-3(2H)-thione, 6-methoxy-2-(2-pyrimidinyl)-1,2-benzisoselenazole-3(2H)-thione, 6-trifluoromethyl-2-(2-pyrimidinyl)-1,2-benzisoselenazole-3(2H)-thione, 7-methoxy-2-(2-pyrimidinyl)-1,2-benzisosenlenazole-3(2H)-thione, 5-chloro-2-(2-pyrimidinyl)-1,2-benzisoselenazole-3(2H)-thione, 5-methoxy-2-(2-pyrimidinyl)-1,2-benzisoselenazole-3(2H)-thione, 5-nitro-2-(2-pyrimidinyl)-1,2-benzisoselenazole-3(2H)-thione, 4-methoxy-2-(2-pyrimidinyl)-1,2-benzisoselenzole-3(2H)-thione, 5,6-dichloro-2-(2-pyrimidinyl)-1,2-benzisoselenazole-3(2H)-thione, 6,7-dichloro-2-(2-pyrimidinyl)-1,2-benzisoselenazole-3(2H)-thione, 6,7-methylenedioxy-2-(2-pyrimidinyl)-1,2-benzisoselenazole-3(2H)-thione, 2-(4-methyl-2-pyrimidinyl)-1,2-benzisoselenazole-3(2H)-thione, 2-(5-nitro-2-pyrimidinyl)-1,2-benzisoselenazole-3(2H)-thione, 2-(4,6-dimethyl-2-pyrimidinyl)-1,2-benzisoselenazole-3(2H)-thione, 2-(2,6-dimethyl-4-pyrimidinyl)-1,2-benzisoselenazole-3(2H)-thione, 2-(6-chloro-2-methylmercapto-4-pyrimidinyl)-1,2-benzisoselenazole-3(2H)-thione, 2-(4-chloro-2-methylmercapto-6-pyrimidinyl)-1,2-benzisoselenazole-3(2H)-thione, 2-(4-chloro-6-methyl-2-pyrimidinyl)-1,2-benzisoselenazole-3(2H)-thione, 2-(6-chloro-3-nitro-2-pyrimidinyl)-1,2-benzisoselenazole-3(2H)-thione, 2-(2-chloro-5-nitro-4-pyrimidinyl-1,2-benzisoselenazole-3(2H)-thione, 2-(4,6-dichloro-2-pyrimidinyl)-1,2-benzisoselenazole-3(2H)-thione, 2-(4,6-dichloro-5-pyrimidinyl)-1,2-benzisoselenazole-3(2H)-thione, 2-(4,6-dimercapto-2-pyrimidinyl)-1,2-benzisoselenazole-3(2H)-thione, 2-(2-benzothiazolyl)-1,2-benzisoselenazole-3(2H)-thione, 2-(4-chloro-2-benzothiazolyl)-1,2-benzisoselenazole-3(2H)-thione, 2-(4-methoxy-2-benzothiazolyl)-1,2-benzisoselenazole-3(2H)-thione, 2-(6-methoxy-2-benzothiazolyl)-1,2-benzisoselenazole-3(2H)-thione, 2-(4-methyl-2-benzothiazolyl)-1,2-benzisoselenazole-3(2H)-thione, 2-(2-methyl-5-benzothiazolyl)-1,2-benzisoselenazole-3(2H)-thione, 2-(6-nitro-2-benzthiazolyl)-1,2-benzisoselenazole-3(2H)-thione, 2-(5,6-dimethyl-2-benzothiazolyl)-1,2-benzisoselenazole-3(2H)-thione, 2-(2-thiazolyl)-1,2-benzisoselenazole-3(2H)-thione, 6-chloro-2-(2-thiazolyl)-1,2-benzisoselenazole-3(2H)-thione, 6-fluoro-2-(2-thiazolyl)-1,2-benzisoselenazole-3(2H)-thione, 6-methyl-2-(2-thiazolyl)-1,2-benzisoselenazole-3(2H)-thione, 6-methoxy-2-(2-thiazolyl)-1,2-benzisoselenazole-3(2H)-thione, 6-trifluoromethyl-2-(2-thiazolyl)-1,2-benzisoselenazole-3(2H)-thione, 7-methoxy-2-(2-thiazolyl)-1,2-benzisoselenazole-3(2H)-thione, 5-chloro-2-(2-thiazolyl)-1,2-benzisoselenazole-3(2H)-thione, 5-methoxy-2-(2-thiazolyl)-1,2-benzisoselenazole-3(2H)-thione, 5-nitro-2-(2-thiazolyl)-1,2-benzisoselenazole-2-(2-thiazolyl)-1,2-benzisoselenazole-3(2H)-thione, 4-methoxy-2-(2-thiazolyl)-1,2-benzisoselenazole-3(2H)-thione, 5,6-dichloro-2-(2-thiazolyl)-1,2-benzisoselenazole-3(2H)-thione, 6,7-dichloro-2-(2-thiazolyl)-1,2-benzisoselenazole-3(2H)-thione, 6,7-methylenedioxy-2-(2-thiazolyl)-1,2-benzisoselenazole-3(2H)-thione, 2-(4-methyl-2-thiazolyl)-1,2-benzisoselenazole-3(2H)-thione, 2-(5-methyl-2-thiazolyl)-1,2-benzisoselenazole-3(2H)-thione, 2-(5-nitro-2-thiazolyl-1,2-benzisoselenazole-3(2H)-thione, 2-(5-chloro-2-thiazolyl)-1,2-benzisoselenazole-3(2H)-thione, 2-(3-methyl-5-isothiazolyl)-1,2-benzisoselenazole-3(2H)-thione, 2-(2-imidazolyl)-1,2-benzisoselenazole-3(2H)-thione, 2-(3-pyrazolyl)-1,2-benzisoselenazole-3(2H)-thione, 2-(1,3,4-thiadiazol-2-yl)-1,2-benzisoselenazole-3(2H)-thione, 2-(5-mercapto-1,3,4-thiadiazol-2-yl)-1,2-benzisoselenazole-3(2H)-thione, 2-(5-methyl-1,3,4-thiadiazol-2-yl)-1,2-benzisoselenazole-3(2H)-thione, 2-(5-trifluoromethyl-1,3,4-thiadiazol-2-yl)-1,2-benzisoselenazole-3(2H)-thione, 2-(5-tert.-butyl-1,3,4-thiadiazol-2-yl)-1,2-benzisoselenazole-3(2H)-thione, 2(2-pyrazinyl)-1,2-benzisoselenazole-3(2H)-thione, 2-(2-pyridazinyl)-1,2-benzisoselenazole-3(2H)-thione, 2-(2-benzimidazolyl)-1,2- benzisoselenazole-3(2H)-thione, 2-(5,6-dimethyl-2-benzimidazolyl)-1,2-benzisoselenazole-3(2H)-thione, 2-(5-benzotriazolyl)-1,2-benzisoselenazole-3(2H)-thione, 2-(7-chloro-1,2,4-benzotriazin-3-yl)-1,2-benzisoselenazole-3(2H)-thione, 2-(1,2,4-benzotriazin-3-yl)-1,2-benzisoselenazole-3(2H)-thione, 2-(7-fluoro-1,2,4-benzotriazin-3-yl)-1,2-benzisoselenazole-3(2H)-thione, 2-(7-nitro-1,2,4-benzotriazin-3-yl)-1,2-benzisoselenazole-3(2H)-thione, 2-(2-benzothienyl)-1,2-benzisoselenazole-3(2H)-thione, 2-(3-benzothienyl)-1,2-benzisoselenazole-3(2H)-thione, 2-(2-thienyl)-1,2-benzisoselenazole-3(2H)-thione, 2-(2,1,3-benzothiadiazol-4-yl)-1,2-benzisoselenazole-3(2H)-thione, 2-(1,2,4-triazin-4-yl)-1,2-benzisoselenazole-3(2H)-thione, 2-(2,6-dimercapto-1,3,5-triazin-4-yl)-1,2-benzisoselenazole-3(2H)-thione, 2-(5,6-dimethyl-1,2,4-triazin-3-yl)-benzisoselenazole-3(2H)-thione, 2-(5,6-diphenyl-1,2,4-triazin-3-yl)-1,2-benzisoselenazole-3(2H)-thione, 2-(1,2,4-triazol-4-yl)-1,2-benzisoselenazole-3(2H)-thione, 2-(5-mercapto-1,2,4-triazol-3-yl)-1,2-benzisoselenazole-3(2H)-thione, 2-(5-tetrazolyl)-1,2-benzisoselenazole-3(2H)-thione, 2-(5-quinolyl)-1,2-benzisoselenazole-3(2H)-thione, 2-(2-methyl-4-quinolyl)-1,2-benzisoselenazole-3(2H)-thione, 2-(6-nitro-5-quinolyl)-1,2-benzisoselenazole-3(2H)-thione, 2-(2-quinolyl)-1,2-benzisoselenazole-3(2H)-thione, 2-(3-quinolyl)-1,2-benzisoselenazole-3(2H)-thione, 2-(8-quinolyl)-1,2-benzisoselenazole-3(2H)-thione, 2-(6-methoxy-8-quinolyl)-1,2-benzisoselenazole-3(2H)-thione, 2-(1-isoquinolyl)-1,2-benzisoselenazole-3(2H)-thione, 2-(5-isoquinolyl)-1,2-benzisoselenazole-3(2H)-thione, 2-(5-indolyl)-1,2-(benzisoselenazole-3(2H)-thione, 2-(5-isoindolyl)-1,2-benzisoselenazole-3(2H)-thione, 2-(5-indazolyl)-1,2-benzisoselenazole-3(2H)-thione, 2-(6-chloro-3-indazolyl)-1,2-benzisoselenazole-3(2H)-thione and 2-(7-indazolyl)-1,2-benzisoselenazole-3(2H)-thione.

The benzisoselenazolethiones of the formula I according to the invention can be used for the treatment of numerous diseases. They are used in particular for the prophylaxis and therapy of infectious diseases to stimulate the immune system and for the therapy of selenium deficiency diseases, such as are defined in W. Kraus and P. Oehme, Das Deut. Gesundheitswesen (The German Health Service), 1979, 34 (37), 1713–1718 and 1979, 34 (37), 1769–1773.

The benziseoselenazolethiones of the formula I are particularly used in the therapy of rheumatic diseases, such as, for example, arthrosis or chronic polyarthritis, the new compounds being distinguished by a good tolerance, since they are non-toxic and, in contrast to known anti-inflammatory therapeutics, show no ulcer formation or gastrointestinal irritation at all.

Therefor, the present invention is further directed to a process for the prophylaxis and therapy of infection diseases, to stimulate the immune system, for the therapy of selenium deficiency diseases and for the therapy of rheumatic diseases comprising administering to the being suffering from such states or diseases a compound according to formula I.

The new benziseoselenazolethiones of the general formula I are obtained in a manner which is known per se. For instance, a compound of the general formula II

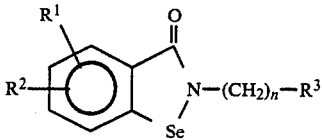

wherein $R^1$, $R^2$ and $R^3$ and n have the meanings given in formula I, is reacted with diphosphorus pentasulphide by heating in a suitable solvent to give the corresponding thione. Aromatic hydrocarbons, such as benzene, toluene or xylene, at temperatures between 70° and 150° C., preferably at 80° at 110° C., are preferred here.

In another process, in which compounds of the general formula II, wherein $R^1$, $R^2$ and $R^3$ and n have the meanings given in formula I, are also used as starting substances, the conversion to the corresponding thione is carried out by the action of 2,4-bis-(4-methoxyphenyl)-2,4-dithioxo-1,3,2,4-dithiadiphosphetane (Lawesson reagent) in an inert solvent, such as toluene or xylene, at temperatures between 70° and 150° C., preferably at 110° C. (E. Shabana et al., Nouv. J. Chim. 4, 47, 1980).

The benzisoselenazolones of the formula II used as starting compounds are either known [compare, for example, R. Lesser and R. Weiss, Ber. 57 (1924), German Offenlegungsschrift No. 3,027,073 and German Offenlegungsschrift No. 3,027,075], or they can be obtained by processes described in these references, by reacting o-chloroselenobenzoyl chlorides of the formula III

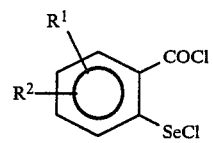

wherein $R^1$ and $R^2$ have the meanings given in formula I, with amines of the formula IV $$R^3-(CH_2)_n-NH_2 \qquad IV$$

wherein $R^3$ and n have the meanings given in formula I.

The corresponding o-chloroselenobenzoyl chlorides are prepared in accordance with the process of A. Ruwet and M. Renson, Bull. Soc. Chim. Belg. 1966, 75, 157–163.

Examples of possible starting compounds of the formula II are: 2-ethyl-1,2-benzisoselenazol-3(2H)-one, 6-chloro-2-ethyl-1,2-benzisoselenazol-3(2H)-one, 6-fluoro-2-ethyl-1,2-benzisoselenazol-3(2H)-one, 6-methyl-2-ethyl-1,2-benzisoselenazol-3(2H)-one, 6-methoxy-2-ethyl-1,2-benzisoselenazol-3(2H)-one, 6-trifluoromethyl-2-ethyl-1,2-benzisoselenazol-3(2H)-one, 7-methoxy-2-ethyl-1,2-benzisoselenazol-3(2H)-one, 5-chloro-2-ethyl-1,2-benzisoselenazol-3(2H)-one, 5-methoxy-2-ethyl-1,2-benzisoselenazol-3-(2H)-one, 5-nitro-2-ethyl-1,2-benzisoselenazol-3(2H)-one, 4-methoxy-2-ethyl-1,2-benzisoselenazol-3(2H)-one, 5,6-dichloro-2-ethyl-1,2-benzisoselenazol-3(2H)-one, 6,7-dichloro-2-ethyl-1,2-benzisoselenazol-3(2H)-one, 6,7-methylenedioxy-2-ethyl-1,2-benzisoselenazol-3-(2H)-one, 2-butyl-1,2-benzisoselenazol-3(2H)-one, 2-(phenylmethyl)-1,2-benzisoselenazol-3(2H)-one, 2-(4-phenylbutyl)-1,2-benzisoselenazol-3(2H)-one, 2-phenyl- 1,2-benzisoselenazol-3(2H)-one, 6-chloro-2-phenyl-1,2-benzisoselenazol-3(2H)-one, 6-fluoro-2-phenyl-1,2-benzisoselenazol-3(2H)-one, 6-methyl-2-phenyl-1,2-benzisoselenazol-3(2H)-one, 6-methoxy-2-phenyl-1,2-benzisoselenazol-3(2H)-one, 6-trifluoromethyl-2-phenyl-1,2-benzisoselenazol-3(2H)-one, 7-methoxy-2-phenyl-1,2-benzisoselenazol-3(2H)-one, 5-chloro-2-phenyl-1,2-benzisoselenazol-3(2H)-one, 5-methoxy-2-phenyl-1,2-benzisoselenazol-3(2H)-one, 5-nitro-2-phenyl-1,2-benzisoselenazol-3(2H)-one, 4-methoxy-2-phenyl-1,2-benzisoselenazol-3(2H)-one, 5,6-dichloro-2-phenyl-1,2-benzisoselenazol-3(2H)-one, 6,7-dichloro-2-phenyl-1,2-benzisoselenazol-3(2H)-one, 6,7-methylenedioxy-2-phenyl-1,2-benzisoselenazol-3(2H)-one, 2-(2-fluorophenyl)-1,2-benzisoselenazol-3-(2H)-one, 2-(3-fluorophenyl)-1,2-benzisoselenazol-3-(2H)-one, 2-(4-fluorophenyl)-1,2-benzisoselenazol-3(2H)-one, 2-(2-chlorophenyl)-1,2-benzisoselenazol-3(2H)-one, 2-(3-chlorophenyl)-1,2-benzisoselenazol-3(2H)-one, 2-(4-chlorophenyl)-1,2-benzisoselenazol-3(2H)-one, 2-(2-trifluoromethylphenyl)-1,2-benzisoselenazol-3-(2H)-one, 2-(3-trifluoromethylphenyl)-1,2-benzisoselenazol-3(2H)-one, 2-(4-trifluoromethylphenyl)-1,2-benzisoselenazol-3(2H)-one, 2-(2-methylphenyl)-1,2-benzisoselenazol-3(2H)-one, 2-(3-methylphenyl)-1,2-benzisoselenazol-3-(2H)-one, 2-(4-methylphenyl)-1,2-benzisoselenazol-3-(2H)-one, 2-(2-methoxyphenyl)-1,2-benzisoselenazol-3(2H)-one, 2-(3-methoxyphenyl)-1,2-benzisoselenazol-3(2H)-one, 2-(4-methoxyphenyl)-1,2-benzisoselenazol-3(2H)-one, 2-(2,4-dimethoxyphenyl)-1,2-benzisoselenazol-3(2H)-one, 2-(2,5-dimethoxyphenyl)-1,2-benzisoselenazol-3(2H)-one, 2-(3,4-dimethoxyphenyl)-1,2-benzisoselenazol-3(2H)-one, 2-(3,5-dimethoxyphenyl)-1,2-benzisoselenazol-3(2H)-one, 2-(2,3-dimethylphenyl)-1,2-benzisoselenazol-3(2H)-one, 2-(2,4-dimethylphenyl)-1,2-benzisoselenazol-3(2H)-one, 2-(2,5-dimethylphenyl)-1,2-benzisoselenazol-3(2H)-one, 2-(2,6-dimethylphenyl)-1,2-benzisoselenazol-3(2H)-one, 2-(3,4-dimethylphenyl)-1,2-benzisoselenazol-3(2H)-one, 2-(3,5-dimethylphenyl)-1,2-benzisoselenazol-3(2H)-one, 2-(2-chloro-4-methylphenyl)-1,2-benzisoselenazol-3(2H)-one, 2-(2-chloro-6-methylphenyl)-1,2-benzisoselenazol-3(2H)-one, 2-(3-chloro-2-methylphenyl)-1,2-benzisoselenazol-3(2H)-one, 2-(3-chloro-4-methylphenyl)-1,2-benzisoselenazol-3(2H)-one, 2-(4-chloro-2-methylphenyl)-1,2-benzisoselenazol-3(2H)-one, 2-(5-chloro-2-methylphenyl)-1,2-benzisoselenazol-3(2H)-one, 2-(5-fluoro-2-methylphenyl)-1,2-benzisoselenazol-3(2H)-one, 2-(4-fluoro-3-methylphenyl)-1,2-benzisoselenazol-3(2H)-one, 2-(4-fluoro-2-methylphenyl)-1,2-benzisoselenazol-3(2H)-one, 2-(3-fluoro-4-methylphenyl)-1,2-benzisoselenazol-3(2H)-one, 2-(2-fluoro-4-methylphenyl)-1,2-benzisoselenazol-3(2H)-one, 2-(3-chloro-4-fluorophenyl)-1,2-benzisoselenazol-3(2H)-one, 2-(4-chloro-3-fluorophenyl)-1,2-benzisoselenazol-3(2H)-one, 2-(2-nitrophenyl)-1,2-benzisoselenazol-3(2H)-one, 2-(3-nitrophenyl)-1,2-benzisoselenazol-3(2H)-one, 2-(4-nitrophenyl)-1,2-benzisoselenazol-3(2H)-one, 2-(4-methoxy-2-nitrophenyl)-1,2-benzisoselenazol-3(2H)-one, 2-(2-methyl-4-nitrophenyl)-1,2-benzisoselenazol-3(2H)-one, 2-(4-methyl-2-nitrophenyl)-1,2-benzisoselenazol-3(2H)-one, 2-(2-methyl-3-nitrophenyl)-1,2-benzososelenazol-3(2H)-one, 2-(2-methyl-5-nitrophenyl)-1,2-benzisoselenazol-3(2H)-one, 2-(3,4-methylenedioxyphenyl)-1,2-benzisoselenazol-3(2H)-one, 2-(2-pyridyl)-1,2-benzisoselenazol-3-(2H)-one, 2-(3-pyridyl)-1,2-benzisoselenazol-3(2H)-one, 2-(4-pyridyl)-1,2-benzisoselenazol-3(2H)-one, 6-chloro-2-(2-pyridyl)-1,2-benzisoselenazol-3(2H)-one, 6-fluoro-2-(2-pyridyl)-1,2-benzisoselenazol-3(2H)-one, 6-methyl-2-(2-pyridyl)-1,2-benzisoselenazol-3(2H)-one, 6-methoxy-2-(2-pyridyl)-1,2-benzisoselenazol-3(2H)-one, 6-trifluoromethyl-2-(2-pyridyl)-1,2-benzisoselenazol-3(2H)-one, 7-methoxy-2-(2-pyridyl)-1,2-benzisoselenazol-3(2H)-one, 5-chloro-2-(2-pyridyl)-1,2-benzisoselenazol-3(2H)-one, 5-methoxy-2-(2-pyridyl)-1,2-benzisoselenazol-3(2H)-one, 5-nitro-2-(2-pyridyl)-1,2-benzisoselenazol-3(2H)-one, 4-methoxy-2-(2-pyridyl)-1,2-benzisoselenazol-3(2H)-one, 5,6-dichloro-2-(2-pyridyl)-1,2-benzisoselenazol-3(2H)-one, 6,7-dichloro-2-(2-pyridyl)-1,2-benzisoselenazol-3(2H)-one, 6,7-methylenedioxy-2-(2-pyridyl)-1,2-benzisoselenazol-3(2H)-one, 2-(2-chloro-3-pyridyl)-1,2-benzisoselenazol-3(2H)-one, 2-(2-methoxy-5-pyridyl)-1,2-benzisoselenazol-3(2H)-one, 2-(3-nitro-2-pyridyl)-1,2-benzisoselenazol-3(2H)-one, 2-(5-nitro-2-pyridyl)-1,2-benzisoselenazol-3(2H)-one, 2-(3-methyl-2-pyridyl)-1,2-benzisoselenazol-3(2H)-one, 2-(4-methyl-2-pyridyl)-1,2-benzisoselenazol-3(2H)-one, 2-(5-methyl-2-pyridyl)-1,2-benzisoselenazol-3(2H)-one, 2-(6-methyl-2-pyridyl)-1,2-benzisoselenazol-3(2H)-one, 2-(3,5-dichloro-2-pyridyl)-1,2-benzisoselenazol-3(2H)-one, 2-(4,6-dimethyl-2-pyridyl)-1,2-benzisoselenazol-3(2H)-one, 2-(5-chloro-2-pyridyl)-1,2-benzisoselenazol-3(2H)-one, 2-(4-chloro-2-pyridyl)-1,2-benzisoselenazol-3(2H)-one, 2-(2-pyrimidinyl)-1,2-benzisoselenazol-3(2H)-one, 6-chloro-2-(2-pyrimidinyl)-1,2-benzisoselenazol-3(2H)-one, 6-fluoro-2-(2-pyrimidinyl)-1,2-benzisoselenazol-3(2H)-one, 6-methyl-2-(2-pyrimidinyl)-1,2-benzisoselenazol-3(2H)-one, 6-methoxy-2-(2-pyrimidinyl)-1,2-benzisoselenazol-3(2H)-one, 6-trifluoromethyl-2-(2-pyrimidinyl)-1,2-benzisoselenazol-3(2H)-one, 7-methoxy-2-(2-pyrimidinyl)-1,2-benzisoselenazol-3(2H)-one, 5-chloro-2-(2-pyrimidinyl)-1,2-benzisoselenazol-3(2H)-one, 5-methoxy-2-(2-pyrimidinyl)-1,2-benzisoselenazol-3(2H)-one, 5-nitro-2-(2-pyrimidinyl)-1,2-benzisoselenazol-3(2H)-one, 4-methoxy-2-(2-pyrimidinyl)-1,2-benzisoselenazol-3(2H)-one, 5,6-dichloro-2-(2-pyrimidinyl)-1,2-benzisoselenazol-3(2H)-one, 6,7-dichloro-2-(2-pyrimidinyl)-1,2-benzisoselenazol-3(2H)-one, 6,7-methylenedioxy-2-(2-pyrimidinyl)-1,2-benzisoselenazol-3(2H)-one, 2-(4-methyl-2-pyrimdinyl)-1,2-benzisoselenazol-3(2H)-one, 2-(5-nitro-2-pyrimidinyl)-1,2-benzisoselenazol-3(2H)-one, 2-(4,6-dimethyl-2-pyrimidinyl)-1,2-benzisoselenazol-3(2H)-one, 2-(2,6-dimethyl-4-pyrimidinyl)-1,2-benzisoselenazol-3(2H)-one, 2-(6-chloro-2-methylmercapto-4-pyrimidinyl)-1,2-benzisoselenazol-3(2H)-one, 2-(4-chloro-2-methylmercapto-6-pyrimidinyl)-1,2-benzisoselenazol-3(2H)-one, 2-(4-chloro-6-methyl-2-pyrimidinyl)-1,2-benzisoselenazol-3(2H)-one, 2-(6-chloro-3-nitro-2-pyrimidinyl)-1,2-benzisoselenazol-3(2H)-one, 2-(2-chloro-5-nitro-4-pyrimidinyl)-1,2-benzisoselenazol-3(2H)-one, 2-(4,6-dichloro-2-pyrimidinyl)-1,2-benzisoselenazol-3(2H)-one, 2-(4,6-dichloro-5-pyrimidinyl)-1,2-benzisoselenazol-3(2H)-one, 2-(4,6-dimercapto-2-pyrimidinyl)-1,2-benzisoselenazol-3(2H)-one, 2-(2-benzothiazolyl)-1,2-benzisoselenazol-3(2H)-one, 2-(4-chloro-2-benzothiazolyl)-1,2-benzisoselenazol-3(2H)-one, 2-(4-methoxy-2-benzothiazolyl)-1,2-benzisoselenazol-3(2H)-one, 2-(6-methoxy-2-benzothiazolyl)-1,2-benzisoselenazol-3(2H)-one, 2-(4-methyl-2-benzothiazolyl)-1,2-benzisoselenazol-3(2H)-one, 2-(2-methyl-5-benzothiazolyl)-1,2-benzisoselenazol-3-(2H)-one, 2-(6-nitro-2-benzothiazolyl)-1,2-benzisoselenazol-3(2H)-one, 2-(5,6-dimethyl-2-benzothiazolyl)-1,2-benzisoselenazol-3(2H)-one, 2-(2-thiazolyl)-1,2-benzisoselenazol-3(2H)-one, 6-chloro-2-(2-thiazolyl)-1,2-benzisoselenazol-3(2H)-one, 6-fluoro-2-(2-thiazolyl)-1,2-benzisoselenazol-3(2H)-one, 6-methyl-2-(2-thiazolyl)-1,2-benzisoselenazol-3(2H)-one, 6-methoxy-2-(2-thiazolyl)-1,2-benzisoselenazol-3(2H)-one, 6-trifluoromethyl-2-(2-thiazolyl)-1,2-benzisoselenazol-3(2H)-one, 7-methoxy-2-(2-thiazolyl)-1,2-benzisoselenazol-3(2H)-one, 5-chloro-2-(2-thiazolyl)-1,2-benzisoselenazol-3(2H)-one, 5-methoxy-2-(2-thiazolyl)-1,2-benzisoselenazol-3(2H)-one, 5-nitro-2-(2-thiazolyl)-1,2-benzisoselenazol-3(2H)-one, 4-methoxy-2-(2-thiazolyl)-1,2-benzisoselenazol-3(2H)-one, 5,6-dichloro-2-(2-thiazolyl)-1,2-benzisoselenazol-3(2H)-one, 6,7-dichloro-2-(2-thiazolyl)-1,2-benzisoselenazol-3(2H)-one, 6,7methylenedioxy-2-(2-thiazolyl)-1,2-benzisoselenazol-3(2H)-one, 2-(4-methyl-2-thiazolyl)-1,2-benzisoselenazol-3(2H)-one, 2-(5-nitro-2-thiazolyl)-1,2-benzisoselenazol-3(2H)-one, 2-(5-chloro-2-thiazolyl)-1,2-benzisoselenazol-3(2H)-one, 2-(3-methyl-5-isothiazolyl)-1,2-benzisoselenazol-3(2H)-one, 2-(2-imidazolyl)-1,2-benzisoselenazol-3(2H)-one, 2-(3-pyrazolyl)-1,2-benzisoselenazol-3(2H)-one, 2-(1,3,4-thiadiazol-2-yl)-1,2-benzisoselenazol-3(2H)-one, 2-(5-mercapto-1,3,4-thiadiazol-2-yl)-1,2-benzisoselenazol-3(2H)-one, 2-(5-methyl-1,3,4-thiadiazol-2-yl)-1,2-benzisoselenazol-3(2H)-one, 2-(5-trifluoromethyl-1,3,4-triadiazol-2-yl)-1,2-benzisoselenazol-3(2H)-one, 2-(5-tert.-butyl-1,3,4-thiadiazol-2-yl)-1,2-benzisoselenazol-3(2H)-one, 2-(2-pyrazinyl)-1,2-benzisoselenazol-3(2H)-one, 2-(2-pyridazinyl)-1,2-benzisoselenazol-3(2H)-one, 2-(2-benzimidazolyl)-1,2-benzisoselenazol-3(2H)-one, 2-(5,6-dimethyl-2-benzimidazolyl)-1,2-benzisoselenazol-3(2H)-one, 2-(5-benzotriazolyl)-1,2-benzisoselenazol-3(2H)-one, 2-(7-chloro-1,2,4-benzotriazin-3-yl)-1,2-benzisoselenazol-3(2H)-one, 2-(1,2,4-benzotriazin-3-yl)-1,2-benzisoselenazol-3(2H)-one, 2-(7-fluoro-1,2,4-benzotriazin-3-yl)-1,2-benzisoselenazol-3(2H)-one, 2-(7-nitro-1,2,4-benzotriazin-3-yl)-1,2-benzisoselenazol-3(2H)-one, 2-(2-benzothienyl)-1,2-benzisoselenazol-3(2H)-one, 2-(3-benzothienyl)-1,2-benzisoselenazol-3(2H)-one, 2-(2-thienyl)-1,2-benzisoselenazol-3(2H)-one, 2-(2,1,3-benzothiadiazol-4-yl)-1,2-benzisoselenazol-3(2H)-one, 2-(1,2,4-triazin-4-yl)-1,2-benzisoselenazol-3(2H)-one, 2-(2,6-dimercapto-1,3,5-triazin-4-yl)-1,2-benzisoselenazol-3(2H)-one, 2(5,6-dimethyl-1,2,4-triazin-3-yl)-1,2-benzisoselenazol-3(2H)-one, 2-(5,6-diphenyl-1,2,4-triazin-3-yl)-1,2-benzisoselenazol-3(2H)-one, 2-(1,2,4-triazol-4-yl)-1,2-benzisoselenazol-3(2H)-one, 2-(5-mercapto-1,2,4-triazol-3-yl)-1,2-benzisoselenazol-3(2H)-one, 2-(5-tetrazolyl)-1,2-benzisoselenazol-3(2H)-one, 2-(5-quinolyl)-1,2-benzisoselenazol-3(2H)-one, 2-(2-methyl-4-quinolyl)-1,2-benzisoselenazol-3(2H)-one, 2-(6-nitro-5-quinolyl)-1,2-benzisoselenazol-3(2H)-one, 2-(2-quinolyl)-1,2-benzisoselenazol-3(2H)-one, 2-(3-quinolyl)-1,2-benzisoselenazol-3(2H)-one, 2-(8-quinolyl)-1,2-benzisoselenazol-3(2H)-one, 2-(6-methoxy-8-quinolyl)-1,2-benzisoselenazol-3(2H)-one, 2-(1-isoquinolyl)-1,2-benzisoselenazol-3(2H)-one, 2-(5-isoquinolyl)-1,2-benzoisoselenazol-3(2H)-one, 2-(5-indolyl)-1,2-benzisoselenazol-3(2H)-one, 2-(5-isoindolyl)-1,2-benzisoselenazol-3(2H)-one, 2-(5-indazolyl)-1,2-benzisoselenazol-3(2H)-one, 2-(6-chloro-3-indazolyl)-1,2-benzisoselenazol-3(2H)-one and 2-(7-indazolyl)-1,2-benzisoselenazol-3(2H)-one.

The benzisoselenazolethiones of the general formula I according to the invention can be processed to pharmaceutical products in the customary manner. To prepare the pharmaceutical products which contain benzisoselenazolethiones of the formula I as the active component, the active compound can be employed as such or in combination with suitable pharmaceutical diluents and/or excipients and formulated in the customary manner.

In the field of human and veterinary medicine, the active compound are administered in any desired form, for example systemically, with the proviso that the development or maintenance of adequate levels of active compound in the blood or tissue is guaranteed. This can be achieved in oral, rectal or parenteral administration in suitable doses. The pharmaceutical formulation of the active compound is advantageously in the form of individual doses which are matched to the desired administration, such as, for example, tablets, dragees, capsules, suppositories, sols or gels. The dosage of the compounds is usually between 10 and 1,000 mg per day, preferably between 30 and 300 mg, and can be administered in one or several portions, preferably two to three portions daily. Suitable excipients which are used for the preparation of agents which can be administered orally, for example in the form of tablets or capsules or in granular or powder form, are, for example, calcium carbonate, calcium phosphate, starch, sugar, lactose, talc, magnesium stearate, gelatine, polyvinylpyrrolidone, gum arabic, sorbitol, microcrystalline cellulose, polyethylene glycol, carboxymethylcellulose, shellac and the like. The tablets can be coated in the customary manner. Liquid formulations for oral administration can be in the form of aqueous or oily suspensions or solutions, in the form of a syrup, an elixir and the like. These are prepared in the customary manner. The injectable formulations can be aqueous or oily suspensions or solutions, pulverulent compositions with a filler and freeze-dried products which are dissolved before use, and the like. These formulations are prepared in the customary manner. The pharmaceutical products according to the invention can also be in the form of suppositories for rectal administration, which can contain pharmaceutically acceptable excipients which are known as such, for example polyethylene glycol, lanolin, cacao butter, Witepsol ® and the like. External products are preferably prepared in the form of ointments or creams, which are prepared in the customary manner using the usual constituents.

The preparation of the compounds according to the invention will be illustrated in more detail by the following examples.

EXAMPLE 1

2-Phenyl-1,2-benzisoselenazole-3(2H)-thione

A mixture of 2.75 g (0.01 mole) of 2-phenyl-1,2-benzisoselenazol-3(2H)-one and 2.06 g (0.0051 mole) of 2,4-bis-(4-methoxyphenyl)-2,4-dithioxo-1,3,2,4-dithiadiphosphetane (LAWESSON reagent) in 15 ml of toluene is heated at 100° C. for 5 hours. After cooling, the solvent is distilled off in vacuo and the oily residue is extracted 3 times with 100 ml of ether/petroleum ether 25:75 (V/V). After the extraction solution has been concentrated, the residue is introduced onto a silica gel column and eluted with toluene/hexane 7:3 (V/V). Yield: 1.71 g (58.7% of theory); melting point: 64°–65° C. (after recrystallisation from ethanol)

The following compounds were prepared analogously to the instructions of Example 1: 2-(4-methylphenyl)-1,2-benzisoselenazole-3(2H)-thione, melting point 55°–56° C., 2-(4-fluorophenyl)-1,2-benzisoselenazole-3(2H)-thione, melting point 67°–69° C., 2-(4-methoxyphenyl)-1,2-benzisoselenazole-3(2H)-thione, melting point 64°–66° C., 2-(4-nitrophenyl)-1,2-benzisoselenazole-3(2H)-thione, melting point 187°–188° C., 2-(4-trifluoromethylphenyl)-1,2-benzisoselenazol-3(2H)-thione, melting point 129° C., 6-fluoro-2-phenyl-1,2-benzisoselenazole-3(2H)-thione, melting point 101°–103° C., 6-methyl-2-phenyl-1,2-benzisoselenazole-3(2H)-thione, melting point 121°–123° C., 6-chloro-2-phenyl-1,2-benzisoselenazole-3(2H)-thione, melting point 159°–161° C., 6-methoxy-2-phenyl-1,2-benzisoselenazole-3(2H)-thione, melting point 121°–122° C., 5-nitro-2-phenyl-1,2-benzisoselenazole-3(2H)-thione, melting point 154° C., 5-chloro-2-phenyl-1,2-benzisoselenazole-3(2H)-thione, melting point 128° C., 7-methoxy-2-phenyl-1,2-benzisoselenazole-3(2H)-thione, melting point 123°–124° C., 6,7-methylenedioxy-2-phenyl-1,2-benzisoselenazole-3(2H)-thione, melting point 73° C., 2-(5-methyl-2-thiazolyl)-1,2-benzisoselenazole-3(2H)-thione, melting point 195°–196° C., 2-(2,6-dimethyl-4-pyrimidinyl)-1,2-benzisoselenazole-3(2H)-thione, melting point 137°–139° C., 2-(4,6-dimethyl-2-pyrimidinyl)-1,2-benzisoselenazole-3(2H)-thione, melting point 162°–163° C., 2-(4,6-dimethyl-2-pyridyl)-1,2-benzisoselenazole-3(2H)-thione, melting point 141°–143° C., 2-(5-chloro-2-pyridyl)-1,2-benzisoselenazole-3(2H)-thione, melting point 171°–173° C., 2-(2-methoxy-5-pyridyl)-1,2-benzisoselenazole-3(2H)-thione, melting point 135°–136° C., 2-(2,6-dichloro-3-pyridyl)-1,2-benzisoselenazole-3(2H)-thione, melting point 101°–102° C., 2-(2-benzothiazolyl)-1,2-benzisoselenazole-3(2H)-thione, melting point 300°–303° C., 2-(2-pyrimidinyl)-1,2-benzisoselenazole-3(2H)-thione, melting point 195°–196° C., 2-(2-thiazolyl)-1,2-benzisoselenazole-3(2H)-thione, melting point 189°–191° C., 2-(4-pyridyl)-1,2-benzisoselenazole-3-(2H)-thione, melting point 171°–174° C., 2-(3-pyridyl)-1,2-benzisoselenazole-3(2H)-thione, melting point 179°–180° C., 2-(2-pyridyl)-1,2-benzisoselenazole-3(2H)-thione, melting point 141°–143° C., 2-(2-chloro-3-pyridyl)-1,2-benzisoselenazole-3(2H)-thione, melting point 102°–103° C. and 2-(2-pyrazinyl)-1,2-benzisoselenazole-3(2H)-thione, melting point 181°–184° C.

EXAMPLE 2

2-(3-Methoxyphenyl)-1,2-benzisoselenazole-3(2H)-thione 7 g (0.03 mole) of diphosphorus pentasulphide are added in small portions to a mixture of 18.3 g (0.06 mole) of 2-(3-methoxyphenyl)-1,2-benzisoselenazol-3(2H)-one in 200 ml of xylene at room temperature, with stirring. The reaction mixture is kept at 80° C. for 7 hours. The clear solution is decanted from the resinous residue and washed first with aqueous sodium bicarbonate solution and then with water. After the solution has been concentrated in vacuo, the residue is recrystallised from ethanol. Yield: 9.95 g (51.6% of theory); melting point 51°–52° C.

The following compounds were prepared analogously to the instructions of Example 2: 2-(2-fluorophenyl)-1,2-benzisoselenazole-3(2H)-thione, melting point 55°–57° C., 2-(3,4-methylenedioxyphenyl)-1,2-benzisoselenazol-3(2H)-thione, melting point 85°–88° C., 2-(phenylmethyl)-1,2-benzisoselenazole-3(2H)-thione, melting point 41° C., 2-(4-phenylbutyl)-1,2-benzisoselenazole-3(2H)-thione, oil, 2-ethyl-1,2-benzisoselenazole-3(2H)-thione, oil, 2-(2-methylphenyl)-1,2-benzisoselenazole-3(2H)-thione, melting point 65°–67° C. and 2-butyl-1,2-benzisoselenazole-3(2H)-thione, oil.

The following compounds are prepared analogously to the instructions of Examples 1 and 2: 6-chloro-2-ethyl-1,2-benzisoselenazole-3(2H)-thione. 6-fluoro-2-ethyl-1,2-benzisoselenazole-3(2H)-thione, 6-methyl-2-ethyl-1,2-benzisoselenazole-3(2H)-thione, 6-methoxy-2-ethyl-1,2-benzisoselenazole-3(2H)-thione, 6-trifluoromethyl-2-ethyl-1,2-benzisoselenazole-3(2H)-thione, 7-methoxy-2-ethyl-1,2-benzisoselenazole-3(2H)-thione, 5-chloro-2-ethyl-1,2-benzisoselenazole-3(2H)-thione, 5-methoxy-2-ethyl-1,2-benzisoselenazole-3(2H)-thione, 5-nitro-2-ethyl-1,2-benzisoselenazole-3(2H)-thione, 4-methoxy-2-ethyl-1,2-benzisoselenazole-3(2H)-thione, 5,6-dichloro-2-ethyl-1,2-benzisoselenazole-3(2H)-thione, 6,7-dichloro-2-ethyl-1,2-benzisoselenazole-3(2H)-thione, 6,7-methylenedioxy-2-ethyl-1,2-benzisoselenazole-3(2H)-thione, 6-trifluoromethyl-2-phenyl-1,2-benzisoselenazole-3(2H)-thione, 5-methoxy-2-phenyl-1,2-benzisoselenazole-3(2H)-thione, 4-methoxy-2-phenyl-1,2-benzisoselenazole-3(2H)-thione, 5,6-dichloro-2-phenyl-1,2-benzisoselenazole-3(2H)-thione, 6,7-dichloro-2-phenyl-1,2-benzisoselenazole-3(2H)-thione, 2-(3-fluorophenyl)-1,2-benzisoselenazole-3(2H)-thione, 2-(2-chlorophenyl)-1,2-benzisoselenazole-3(2H)-thione, 2-(3-chlorophenyl)-1,2-benzisoselenazole-3(2H)-thione, 2-(4-chlorophenyl)-1,2-benzisoselenazole-3(2H)-thione, 2-(4-chlorophenyl)-1,2-benzisoselenazole-3(2H)-thione, 2-(2-trifluoromethylphenyl)-1,2-benzisoselenazole-3(2H)-thione, 2-(3-trifluoromethylphenyl)-1,2-benzisoselenazole-3(2H)-thione, 2-(3-methylphenyl)-1,2-benzisoselenazole-3(2H)-thione, 2-(2-methoxyphenyl)-1,2-benzisoselenazole-3(2H)-thione, 2-(2,4-dimethoxyphenyl)-1,2-benzisoselenazole-3(2H)-thione, 2-(2,5-dimethoxyphenyl)-1,2-benzisoselenazole-3(2H)-thione, 2-(3,4-dimethoxyphenyl)-1,2-benzisoselenazole-3(2H)-thione, 2-(3,5-dimethoxyphenyl)-1,2-benzisoselenazole-3(2H)-thione, 2-(2,3-dimethylphenyl)-1,2-benzisoselenazole-3(2H)-thione, 2-(2,4-dimethylphenyl)-1,2-benzisoselenazole-3(2H)-thione, 2-(2,5-dimethylphenyl)-1,2-benzisoselenazole-3(2H)-thione, 2-(2,6-dimethylphenyl)-1,2-benzisoselenazole-3(2H)-thione, 2-(3,4-dimethylphenyl)-1,2-benzisoselenazole-3(2H)-thione, 2-(3,5-dimethylphenyl)-1,2-benzisoselenazole-3(2H)-thione, 2-(2-chloro-4-methylphenyl)-1,2-benzisoselenazole-3(2H)-thione, 2-(2-chloro-6-methylphenyl)-1,2-benzisoselenazole-3(2H)-thione, 2-(3-chloro-2-methylphenyl)-1,2-benzisoselenazole-3(2H)-thione, 2-(3-chloro-4-methylphenyl)-1,2-benzisoselenazole-3(2H)-thione, 2-(4-chloro-2-methylphenyl)-1,2-benzisoselenazole-3(2H)-thione, 2-(5-chloro2-methylphenyl)-1,2-benzisoselenazole-3(2H)-thione, 2-(5-fluoro-2-methylphenyl)-1,2-benzisoselenazole-3(2H)-thione, 2-(4-fluoro-3-methylphenyl)-1,2-benzisoselenazole-3(2H)-thione, 2-(4-fluoro-2-methylphenyl)-1,2-benzisoselenazole-3(2H)-thione, 2-(3-fluoro-4-methylphenyl)-1,2-benzisoselenazole-3(2H)-thione, 2-(2-fluoro-4-methylphenyl)-1,2-benzisoselenazole-3(2H)-thione, 2-(3-chloro-4-fluorophenyl)-1,2-benzisoselenazole-3(2H)-thione, 2-(4-chloro-3-fluorophenyl)-1,2-benzisoselenazole-3(2H)-thione, 2-(2-nitrophenyl)-1,2-benzisoselenazole-3(2H)-thione, 2-(3-nitrophenyl)-1,2-benzisoselenazole-3(2H)-thione, 2-(4-methoxy-2-nitrophenyl)-1,2-benzisoselenazole-3(2H)-thione, 2-(2-methyl-4-nitrophenyl)-1,2-benzisoselenazole-3(2H)-thione, 2-(4-methyl-2-nitrophenyl)-1,2-benzisoselenazole-3(2H)-thione, 2-(2-methyl-3-nitrophenyl)-1,2-benzisoselenazole-3(2H)-thione, 2-(2-methyl-5-nitrophenyl)-1,2-benzisoselenazole-3(2H)-thione, 6-chloro-2-(2-pyridyl)-1,2-benzisoselenazole-3(2H)-thione, 6-fluoro-2-(2-pyridyl)-1,2-benzisoselenazole-3(2H)-thione, 6-methyl-2-(2-pyridyl)-1,2-benzisoselenazole-3(2H)-thione, 6-methoxy-2-(2-pyridyl)-1,2-benzisoselenazole-3(2H)-thione, 6-trifluoromethyl-2-(2-pyridyl)-1,2-benzisoselenazole-3(2H)-thione, 7-methoxy-2-(2-pyridyl)-1,2-benzisoselenazole-3(2H)-thione, 5-chloro-2-(2-pyridyl)-1,2-benzisoselenazole-3(2H)-thione, 5-methoxy-2-(2-pyridyl)-1,2-benzisoselenazole-3(2H)-thione, 5-nitro-2-(2-pyridyl)-1,2-benzisoselenazole-3(2H)-thione, 4-methoxy-2-(2-pyridyl)-1,2-benzisoselenazole-3(2H)-thione, 5,6-dichloro-2-(2-pyridyl)-1,2-benzisoselenazole-3(2H)-thione, 6,7-dichloro-2-(2-pyridyl)-1,2-benzisoselenazole-3(2H)-thione, 6,7-methylenedioxy-2-(2-pyridyl)-1,2-benzisoselenazole-3(2H)-thione, 2-(3-nitro-2-pyridyl)-1,2-benzisoselenazole-3(2H)-thione, 2-(5-nitro-2-pyridyl)-1,2-benzisoselenazole-3(2H)-thione, 2-(3-methyl-2-pyridyl)-1,2-benzisoselenazole-3(2H)-thione, 2-(4-methyl-2-pyridyl)-1,2-benzisoselenazole-3(2H)-thione, 2-(5-methyl-2-pyridyl)-1,2-benzisoselenazole-3(2H)-thione, 2-(6-methyl-2-pyridyl)-1,2-benzisoselenazole-3(2H)-thione, 2-(3,5-dichloro-2-pyridyl)-1,2-benzisoselenazole-3(2H)-thione, 2-(4-chloro-2-pyridyl)-1,2-benzisoselenazole-3(2H)-thione, 6-chloro-2-(2-pyrimidinyl)-1,2-benzisoselenazole-3(2H)-thione, 6-fluoro-2-(2-pyrimidinyl)-1,2-benzisoselenazole-3(2H)-thione, 6-methyl-2-(2-pyrimidinyl)-1,2-benzisoselenazole-3(2H)-thione, 6-methoxy-2-(2-pyrimidinyl)-1,2-benzisoselenazole-3(2H)-thione, 6-trifluoromethyl-2-(2-pyrimidinyl)-1,2-benzisoselenazole-3(2H)-thione, 7-methoxy-2-(2-pyrimidinyl)-1,2-benzisoselenazole-3(2H)-thione, 5-chloro-2-(2-pyrimidinyl)-1,2-benzisoselenazole-3(2H)-thione, 5-methoxy-2-(2-pyrimidinyl)-1,2-benzisoselenazole-3(2H)-thione, 5-nitro-2-(2-pyrimidinyl)-1,2-benzisoselenazole-3(2H)-thione, 4-methoxy-2-(2-pyrimidinyl)-1,2-benzisoselenazole-3(2H)-thione, 5,6-dichloro-2-(2-pyrimidinyl)-1,2-benzisoselenazole-3(2H)-thione, 6,7-dichloro-2-(2-pyrimidinyl)-1,2-benzisoselenazole-3(2H)-thione, 6,7-methylenedioxy-2-(2-pyrimidinyl)-1,2-benzisoselenazole-3(2H)-thione, 2-(4-methyl-2-pyrimidinyl)-1,2-benzisoselenazole-3(2H)-thione, 2-(5-nitro-2-pyrimidinyl)-1,2-benzisoselenazole-3(2H)-thione, 2-(6-chloro-2-methylmercapto-4-pyrimidinyl)-1,2-benzisoselenazole-3(2H)-thione, 2-(4-chloro-2-methylmercapto-6-pyrimidinyl)-1,2-benzisoselenazole-3(2H)-thione, 2-(4-chloro-6-methyl-2-pyrimidinyl)-1,2-benzisoselenazole-3(2H)-thione, 2-(6-chloro-3-nitro-2-pyrimidinyl)-1,2-benzisoselenazole-3(2H)-thione, 2-(2-chloro-5-nitro-4-pyrimidinyl)-1,2-benzisoselenazole-3(2H)-thione, 2-(4,6-dichloro-2-pyrimidinyl)-1,2-benzisoselenazole-3(2H)-thione, 2-(4,6-dichloro-5-pyrimidinyl)-1,2-benzisoselenazole-3(2H)-thione, 2-(4,6-dimercapto-2-pyrimidinyl)-1,2-benzisoselenazole-3(2H)-thione, 2-(4-chloro-2-benzothiazolyl)-1,2-benzisoselenazole-3(2H)-thione, 2-(4-methoxy-2-benzothiazolyl)-1,2-benzisoselenazole-3(2H)-thione, 2-(6-methoxy-2-benzothiazolyl)-1,2-benzisoselenazole-3(2H)-thione, 2-(4-methyl-2-benzothiazolyl)-1,2-benzisoselenazole-3(2H)-thione, 2-(2-methyl-5-benzothiazolyl)-1,2-benzisoselenazole-3(2H)-thione, 2-(6-nitro-2-benzothiazolyl)-1,2-benzoisoselenazole-3(2H)-thione, 2-(5,6-dimethyl-2-benzothiazolyl)-1,2-benzisoselenazole-3(2H)-thione, 6-chloro-2-(2-thiazolyl)-1,2-benzisoselenazole-3(2H)-thione, 6-fluoro-2-(2-thiazolyl)-1,2-benzisoselenazole-3(2H)-thione, 6-methyl-2-(2-thiazolyl)-1,2-benzisoselenazole-3(2H)-thione, 6-methoxy-2-(2-thiazolyl)-1,2-benzisoselenazole-3(2H)-thione, 6-trifluoromethyl-2-(2-thiazolyl)-1,2-benzisoselenazole-3(2H)-thione, 7-methoxy-2-(2-thiazolyl)-1,2-benzisoselenazole-3(2H)-thione, 5-chloro-2-(2-thiazolyl)-1,2-benzisoselenazole-3(2H)-thione, 5-methoxy-2-(2-thiazolyl)-1,2-benzisoselenazole-3(2H)-thione, 5-nitro-2-(2-thiazolyl)-1,2-benzisoselenazole-3(2H)-thione, 4-methoxy-2-(2-thiazolyl)-1,2-benzisoselenazole-3(2H)-thione, 5,6-dichloro-2-(2-thiazolyl)-1,2-benzisoselenazole-3(2H)-thione, 6,7-dichloro-2-(2-thiazolyl)-1,2-benzisoselenazole-3(2H)-thione, 6,7-methylenedioxy-2-(2-thiazolyl)-1,2-benzisoselenazole-3(2H)-thione, 2-(4-methyl-2-thiazolyl)-1,2-benzisoselenazole-3(2H)-thione, 2-(5-nitro-2-thiazolyl)-1,2-benzisoselenazole-3(2H)-thione, 2-(5-chloro-2-thiazolyl)-1,2-benzisoselenazole-3(2H)-thione, 2-(3-methyl-5-isothiazolyl)-1,2-benzisoselenazole-3(2H)-thione, 2-(2-imidazolyl)-1,2-benzisoselenazole-3(2H)-thione, 2-(3-pyrazolyl)-1,2-benzisoselenazole-3(2H)-thione, 2-(1,3,4-thiadiazol-2-yl)-1,2-benzisosleneazole-3(2H)-thione, 2-(5-mercapto-1,3,4-thiadiazol-2-yl)-1,2-benzisoselenazole-3(2H)-thione, 2-(5-trifluoromethyl-1,3,4-thiadiazol-2-yl)-1,2-benzisoselenazole-3(2H)-thione, 2-(5-tert.-butyl-1,3,4-thiadiazol-1,2-benzisoselenazole-3(2H)-thione, 2-(2-pyridazinyl)-1,2-benzisoselenazole-3(2H)-thione, 2-(2-benzimidazolyl)-1,2-benzisoselenazole-3(2H)-thione, 2-(5,6-dimethyl-2-benzimidazolyl)-1,2-benzisoselenazole-3(2H)-thione, 2-(5-benzotriazolyl)-1,2-benzisoselenazole-3(2H)-thione, 2-(7-chloro-1,2,4-benzotriazin-3-yl)-1,2-benzisoselenazole-3(2H)-thione, 2-(1,2,4-benzotriazin-3-yl)-1,2-benzisoselenazole-3(2H)-thione, 2-(7-fluoro-1,2,4-benzotriazin-3-yl)-1,2-benzisoselenazole-3(2H)-thione, 2-(7-nitro-1,2,4-benzotriazin-3-yl)-1,2-benzisoselenazole-3(2H)-thione, 2-(2-benzothienyl)-1,2-benzisoselenazole-3(2H)-thione, 2-(3-benzothienyl)-1,2-benzisoselenazole-3(2H)-thione, 2-(2-thienyl)-1,2-benzisoselenazole-3(2H)-thione, 2-(2,1,3-benzothiadiazol-4-yl)-1,2-benzisoselenazole-3(2H)-thione, 2-(1,2,4-triazin-4-yl)-1,2-benzisoselenazole-3(2H)-thione, 2-(2,6-dimercapto-1,3,5-triazin-4-yl)-1,2-benzisoselenazole-3(2H)-thione, 2-(5,6-dimethyl-1,2,4-triazin-3-yl)-1,2-benzisoselenazole-3(2H)-thione, 2-(5,6-diphenyl-1,2,4-triazin-3-yl)-1,2-benzisoselenazole-3(2H)-thione, 2-(1,2,4-triazol-4-yl)-1,2-benzisoselenazole-3(2H)-thione, 2-(5-mercapto-1,2,4-triazol-3-yl)-1,2-benzisoselenazole-3(2H)-thione, 2-(5-tetrazolyl)-1,2-benzisoselenazole-3(2H)-thione, 2-(5-quinolyl)-1,2-benzisoselenazole-3(2H)-thione, 2-(2-methyl-4-quinolyl)-1,2-benzisoselenazole-3(2H)-thione, 2-(6-nitro-5-quinolyl)-1,2-benzisoselenazole-3(2H)-thione, 2-(2-quinolyl)-1,2-benzisoselenazole-3(2H)-thione, 2-(3-quinolyl)-1,2-benzisoselenazole-3(2H)-thione, 2-(8-quinolyl)-1,2-benzisoselenazole-3(2H)-thione, 2-(6-methoxy-8-quinolyl)-1,2-benzisoselenazole-3(2H)-thione, 2-(1-isoquinolyl)-1,2-benzisoselenazole-3(2H)-thione, 2-(5-isoquinolyl)-1,2-benzisoselenazole-3(2H)-thione, 2-(5-indolyl)-1,2-benzisoselenazole-3(2H)-thione, 2-(5-isoindolyl)-1,2-benzisoselenazole- 3(2H)-thione, 2-(5-indazolyl)-1,2-benzisoselenazole-3(2H)-thione, 2-(6-chloro-3-indazolyl)-1,2-benzisoselenazole-3(2H)-thione and 2-(7-indazolyl)-1,2-benzisoselenazole-3(2H)-thione.

What we claim is:

1. Benzisoselenazolethiones of the general formula I

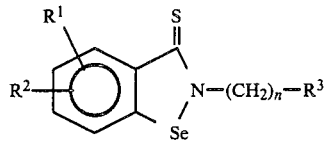

wherein $R^1$ and $R^2$ which can be identical or different, independently of one another are members selected from the group consisting of hydrogen, halogen, $C_1$–$C_4$-alkyl, $C_1$–$C_4$-alkoxy, trifluoromethyl and nitro, and, $R^1$ and $R^2$ together, methylenedioxy, n is zero or an integer from 1 to 4, $R^3$ is a member selected from the group consisting of hydrogen, unsubstituted phenyl, the phenyl groups monosubstituted and those disubstituted by a member selected from the group consisting of halogen, alkyl, alkoxy, trifluoromethyl, nitro and methylenedioxy, and the heterocyclic groups selected from the group consisting of the unsubstituted thiophene, thiazole, isothiazole, imidazole, pyrazole, thiadiazole, pyridine, pyrimidine, pyrazine, pyridazine, benzothiazole, benzimidazole, benzotriazine, benzothiophene, benzothiadiazole, triazine, triazole, tetrazole, quinoline, isoquinoline, indole and indazole groups and such groups being monosubstituted by a member of the group consisting of halogen, $C_1$–$C_4$-alkyl, $C_1$–$C_4$-alkoxy, mercapto, $C_1$–$C_4$-alkylmercapto, phenyl, nitro and trifluoromethyl, and such groups being identically or differently disubstituted by a member of the group consisting of halogen, $C_1$–$C_4$-alkyl, $C_1$–$C_4$-alkoxy, mercapto, $C_1$–$C_4$-alkylmercapto, phenyl, nitro and trifluoromethyl.

2. Benzisoselenazolethiones as claimed in claim 1, wherein $R^1$ and $R^2$, which can be identical or different, independently of one another are members selected from the group consisting of hydrogen, fluorine, chlorine, methyl, methoxy, nitro and tifluoromethyl and, $R^1$ and $R^2$ together, methylenedioxy, and n is an integer from 2 to 4, and $R^3$ is hydrogen.

3. Benzisoselenazolethiones as claimed in claim 1, wherein $R^1$ and $R^2$, which can be identical or different, independently of one another are members selected from the group consisting of hydrogen, fluorine, chlorine, methoxy, nitro and trifluoromethyl and $R^1$ and $R^2$ together, methylenedioxy and n is zero or an integer from 1 to 4, and $R^3$ is a member selected from the group consisting of the unsubstituted groups and the phenyl groups which are identically or differently monosubstituted or disubstituted by fluorine, chlorine, methyl, methoxy, nitro, trifluoromethyl and methylenedioxy.

4. Benzisoselenazolethiones as claimed in claim 1, wherein $R^1$ and $R^2$, which can be identical or different, independently of one another are members selected from the group consisting of hydrogen, fluorine, chlorine, methyl, methoxy, nitro and trifluoromethyl and, $R^1$ and $R^2$ together, methylenedioxy and n is zero, whilst $R^3$ is a member selected from the group consisting of the unsubstituted thiophene, thiazole, isothiazole, imidazole, pyrazole, thiadiazole, pyridine, pyrimidine, pyrazine, pyridazine, benzothiazole, benzimidazole, triazine, triazole and tetrazole groups and such groups monosubstituted and such groups disubstituted by identical or different substituents selected from the group consisting of fluorine, chlorine, methyl, ethyl, butyl, methoxy, ethoxy, mercapto, methylmercapto, ethylmercapto, nitro, phenyl and trifluoromethyl.

* * * * *